US008080430B2

(12) United States Patent
Imamura et al.

(10) Patent No.: US 8,080,430 B2
(45) Date of Patent: Dec. 20, 2011

(54) TARGET SUBSTANCE DETECTION MATERIAL AND METHOD AND KIT FOR DETECTING TARGET SUBSTANCE

(75) Inventors: Takeshi Imamura, Chigasaki (JP); Tetsunori Ojima, Kawasaki (JP); Kazumichi Nakahama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 490 days.

(21) Appl. No.: 11/697,856

(22) Filed: Apr. 9, 2007

(65) Prior Publication Data

US 2007/0248987 A1    Oct. 25, 2007

(30) Foreign Application Priority Data

Apr. 25, 2006  (JP) .................................. 2006-120480

(51) Int. Cl.
*G01N 33/553*  (2006.01)
(52) U.S. Cl. ..................................... 436/525; 435/287.2
(58) Field of Classification Search .......................... None
See application file for complete search history.

(56) References Cited

U.S. PATENT DOCUMENTS

| 5,436,161 | A | * | 7/1995 | Bergstrom et al. .............. 422/57 |
| 7,402,441 | B2 | | 7/2008 | Lowe et al. |
| 2004/0146500 | A1 | | 7/2004 | Miyata et al. |

FOREIGN PATENT DOCUMENTS

| JP | 11-032791 A | 2/1999 |
| JP | 11-101799 A | 4/1999 |
| JP | 2000-146967 A | 5/2000 |
| JP | 2004-325192 A | 11/2004 |
| JP | 2004-346177 A | 12/2004 |
| JP | 2005-522703 A | 7/2005 |
| WO | 02/090990 A1 | 11/2002 |

OTHER PUBLICATIONS

R. M. Hodge et al., "Water Absorption and States of Water in Semicrystalline Poly(vinyl alcohol) Films," 37(8) Polymer 37, 1371-76 (1996).
Wei-Zhong Zhang et al., "A Differential Scanning Calorimetry Study of the States of Water in Swollen Poly(vinyl alcohol) Membranes Containing Nonvolatile Additives," 42 J. Membrane Sci. 303-14 (1989).
S.G. Shoemaker et al., "Synthesis and Properties of Vinyl Monomer/Enzyme Conjugates: Conjugation of L-Asparaginase with N-Succinimidyl Acrylate," 15 Appl. Biochem. Biotech. 11-24 (1987).
Takashi Miyata et al., "A Reversibly Antigen-Responsive Hydrogel," 399 Nature 766-69 (1999).

* cited by examiner

*Primary Examiner* — Chris L Chin
(74) *Attorney, Agent, or Firm* — Fitzpatrick, Cella, Harper & Scinto

(57) ABSTRACT

In the present invention, a target substance detection material, which includes a metal structure, a target substance capturing unit, and a polymer matrix retaining the metal structure and the target substance capturing unit, captures a target substance, and as a result, the volume of the polymer matrix is changed. Such a change in the volume of the polymer matrix is measured as a change in the optical properties of the metal structure, and the target is detected. Thereby, the present invention provides a target substance detection material having good operability and high performance, which includes a metal structure as a labeled form, and a target substance detection method for detecting the presence or absence of a target substance in a specimen and/or the concentration thereof, using the material.

5 Claims, 4 Drawing Sheets

TARGET SUBSTANCE DETECTION MATERIAL AND METHOD AND KIT FOR DETECTING TARGET SUBSTANCE

BACKGROUND OF THE INVENTION

1. Field of the Invention

The present invention relates to a target substance detection material and a target substance detection method, which are used to detect a target substance contained in a specimen.

2. Description of the Related Art

In general, a method for specifically detecting the presence or absence of a target substance contained in a specimen or the concentration thereof using an antigen-antibody reaction, which is known as immunological test or immunoassay, is used in many tests. Examples of a test using such a detection method include: xenodiagnosis for detecting viruses or bacteria causing infectious diseases, or disease marker molecules; environmental inspection for detecting harmful substances such as endocrine disrupting chemicals or dioxins existing in the environment; and food inspection for detecting allergenic substances or bacteria existing in food.

In such inspections, a method for detecting the presence or absence of a target substance or the concentration thereof with high sensitivity by substituting them with the presence or absence of a so-called "labeled form" or the concentration thereof is adopted in many cases. Such a labeled form includes a case of being indirectly detected (indirect labeled form) and a case of being directly detected (direct labeled form). An indirect labeled form is used in the enzyme immunoassay (EIA) method, the chemiluminescent immunoassay (CLIA) method, or the electrochemiluminescence immunoassay (ECLIA) method. That is to say, such an indirect labeled form is used to measure the presence or absence of a substance that is indirectly converted by a labeled form, or the concentration thereof. A direct labeled form is a labeled form used in direct detection of the presence or absence of a labeled form itself or the concentration thereof, such as a case where the labeled form is a fluorochrome or latex label.

In addition, one example of the "labeled form" is an aggregated labeled form. As with colored latex used in the latex assay, the aggregation degree of an aggregated labeled form is increased as the concentration of a target substance is increased. Thus, such an aggregated labeled form is used in a method of detecting the presence or absence of a target substance or the concentration thereof by reading a change in the optical properties thereof.

In recent years, a fine gold or silver particle having a diameter between several nanometers and several hundreds of nanometers has been used for the direct labeled form and the aggregated labeled form among the aforementioned labeled forms.

By an optical effect known as localized surface plasmon resonance, such a fine gold or silver particle having a diameter between several nanometers and several hundreds of nanometers generally has the property of absorbing light between approximately 450 and 650 nanometers, and it is colored in a visible region. It has been known that, with regard to absorption of light due to localized surface plasmon resonance, the strength or absorption wavelength thereof is changed by the positional relationship between fine particles. In addition, when compared with the previously used labeled forms, since such a fine gold or silver particle does not have discoloration towards fluorescent labeling, and also since such a fine particle is very advantageous in that the particle size thereof is smaller than that of latex and in that a reaction efficiency is high, such a fine gold or silver particle has been used as the aforementioned direct labeled form or aggregated labeled form in many cases.

Japanese Patent Application Laid-Open No. H11-032791 discloses a detection method using antibody-sensitized colloidal gold produced by allowing colloidal gold particles to be adsorbed on an antibody. Such antibody-sensitized colloidal gold is prepared, and the antibody-sensitized colloidal gold is allowed to react with an antigen group containing a test antigen. Thereafter, the reaction product is washed, and a red test antigen, to which the antibody-sensitized colloidal gold has been fixed, is detected by visual observation.

Japanese Patent Application Laid-Open Nos. H11-101799 and 2000-146967 disclose a method of enhancing the safety of a reagent solution containing antibody-sensitized metal colloid, which is used in measurement methods such as an immunochromatography method or an agglutination calorimetric method using such antibody-sensitized metal colloid as a labeled form. In the immunochromatography method, an antigen/antibody-metal colloid complex formed by allowing antibody-sensitized metal colloid to react with an antigen is electrophoresed on a determination paper (film). The complex is captured by the antibody immobilized on the determination paper on which an antibody is immobilized, and coloration due to the metal colloid generated as a result of such capture is then determined, so as to examine the presence or absence of an antigen. In the agglutination calorimetric method, a change in color tone generated as a result of agglutination of gold colloid when antibody-sensitized gold colloid is allowed to react with an antigen in a solution is defined as a change in absorbance, and such a change is measured, so as to examine the presence or absence of an antigen or the amount thereof. It is considered that the enhancement of the safety of a reagent solution containing gold colloidal particles used in these methods contributes to the improvement of measurement precision.

Japanese Patent Application Laid-Open No. 2004-325192 discloses a method of measuring a hapten suitable for automation that does not need B/F separation, which has good measurement sensitivity and wherein the measurement time is reduced, and a measurement kit based on the above measurement method. This method of measuring the amount of a hapten in a specimen includes the following steps. First, a specimen containing an antigen is mixed with a first reagent containing a hapten-binding protein. Then, a second reagent containing an antihapten antibody-binding gold colloid is added to the obtained mixed solution, and they are then mixed. Thereafter, a change in absorbance due to an immune agglutination reaction occurring between the hapten-binding protein and the antihapten antibody-binding gold colloid is obtained based on absorbance measured two or more times at a wavelength between 500 nm and 580 nm. Otherwise, such a change in absorbance is obtained based on absorbance measured two or more times at a dual-wavelength, namely, at a dominant wavelength between 500 nm and 580 nm and at a subwavelength between 620 nm and 800 nm.

Japanese Patent Application Laid-Open No. 2004-346177 describes a method of detecting a target substance using an imprinted polymer on which a gold nanoparticle is immobilized. In this detection method, a target substance is detected by utilizing a change in the expansion coefficient of an imprinted polymer generated as a result of the action of the imprinted polymer to capture the target substance. When the expansion coefficient of the imprinted polymer is changed, the distance between gold nanoparticles immobilized on the imprinted polymer is changed, so that signals derived from the gold nanoparticles are also changed. Utilizing such a change in the signals, the target substance can be detected.

Japanese Patent Application Laid-Open Nos. H11-032791, H11-101799, 2000-146967 and 2004-325192 describe test methods, in which the characteristics of the aforementioned fine gold or silver particles are utilized. However, since an antibody acting as a target substance capturing unit is immobilized on the surface of such a fine gold or silver particle in these methods, a phenomenon such as agglutination or precipitation is likely to occur depending on conditions. Such a phenomenon may affect the reproducibility or precision of the test.

In the detection method described in Japanese Patent Application Laid-Open No. 2004-346177, a change in the expansion coefficient of an imprinted polymer obtained when it captures a target substance is small, and thus it is considered to be difficult to conduct measurement with high sensitivity.

SUMMARY OF THE INVENTION

Taking into consideration the aforementioned problems of prior art techniques, it is an object of the present invention to provide a target substance detection material and a target substance detection method, which have good operability and high performance, and wherein a fine particle containing metal such as gold or silver is used as a labeled form.

The present invention relates to a target substance detection material for detecting a target substance in a specimen, which comprises: a metal structure, a polymer matrix, a target substance capturing unit and a capturing unit binding substance, wherein the target substance capturing unit and the capturing unit binding substance are immobilized on different portions of the polymer matrix and an affinity binding is formed between the capturing unit binding substance and the target substance capturing unit. The dissociation constant between the target substance capturing unit and the capturing unit binding substance can be greater than the dissociation constant between the target substance capturing unit and the target substance.

The polymer matrix can be comprised of a hydrogel.

The above immobilization can be an formed via a covalent bond.

The present invention relates to a target substance detection material for detecting a target substance in a specimen, which comprises: a metal structure, a polymer matrix, a first target substance capturing unit, and a second target substance capturing unit, wherein the first target substance capturing unit and the second target substance capturing unit are immobilized on different portions of the polymer matrix, and the first target substance capturing unit and the second target substance capturing unit have a binding site for different regions of the target substance, respectively.

The polymer matrix can be comprised of a hydrogel.

The above immobilization can be formed via a covalent bond.

The present invention relates to a target substance detection method for detecting a target substance in a specimen, which comprises the steps of: bringing a specimen which contains a target substance into contact with a target substance detection material which comprises a metal structure, a polymer matrix, a target substance capturing unit and a capturing unit binding substance wherein the capturing unit and the binding substance are immobilized on different portions of the polymer matrix and an affinity binding is formed between the capturing unit binding substance and the target substance capturing, to eliminate the affinity binding between the capturing unit binding substance and the target substance capturing unit because of preferential forming of a binding between the target substance capturing unit and the target substance, thereby increasing the volume of the polymer matrix comprised in the target substance detection material, and detecting an optical property of the target substance detection material.

The present invention relates to a target substance detection method for detecting a target substance in a specimen, which comprises the steps of: bringing a specimen which contains a target substance into contact with a target substance detection material which comprises a metal structure, a polymer matrix, a first target substance capturing unit and a second target substance capturing unit wherein the first and second capturing units are immobilized on different portions of the polymer matrix and have a binding site for different regions of the target substance, to make the first and second target substance capturing units capture different regions of the target substance, thereby decreasing the volume of the polymer matrix comprised in the target substance detection material, and detecting an optical property of the target substance detection material.

In addition, the present invention also relates to a material for detecting a target substance in a specimen, which includes a support on which a target substance capturing unit and a capturing unit binding substance having an affinity with the target substance capturing unit are immobilized, and a metal-containing structure, wherein the volume of the support is changed due to the presence or absence of the target substance, and the change is detected based on the properties of the metal-containing structure.

Moreover, the present invention also relates to a material for detecting a target substance in a specimen, which includes a support on which a first target substance capturing unit and a second target substance capturing unit are immobilized, and a metal-containing structure, wherein the first target substance capturing unit and the second target substance capturing unit capture different regions of the target substance, and the volume of the support is changed due to the presence or absence of the target substance, and the change is detected based on the properties of the metal-containing structure.

Furthermore, the present invention also relates to a target substance detection method for detecting the presence or absence of a target substance in a specimen and/or the concentration thereof, which includes: allowing the specimen containing the target substance to come into contact with the target substance detection material, detecting the optical properties of the target substance detection material before and after the contact, and comparing the detection results obtained before the contact with the detection results obtained after the contact.

Still further, the present invention also relates to a target substance detection kit for detecting the presence or absence of a target substance in a specimen and/or the concentration thereof, which includes the target substance detection material and a vessel for allowing the specimen containing the target substance to come into contact with the target substance detection material.

Still further, the present invention also relates to a target substance detection element for detecting the presence or absence of a target substance in a specimen and/or the concentration thereof, which includes the target substance detection material, a region in which the specimen is introduced, a region for allowing the specimen containing the target substance to come into contact with the target substance detection material, and a wavelength light transmitting region for measuring the optical properties of the target substance detection material.

Further features of the present invention will become apparent from the following description of exemplary embodiments with reference to the attached drawings.

DESCRIPTION OF THE EMBODIMENTS

The target substance detection material of the present invention is a material for detecting a target substance in a specimen. The above target substance detection material includes at least a metal structure, a target substance capturing unit, and a polymer matrix that retains the metal structure and the target substance capturing unit. The target substance capturing unit captures the target substance, so that the volume of the polymer matrix can be changed. Such a change in the volume of the polymer matrix is measured as a change in the optical properties of the metal structure, so as to detect the target substance.

The first target substance detection material of the present invention includes at least a target substance capturing unit, a capturing unit binding substance having an affinity with the target substance capturing unit, a metal structure, and a polymer matrix.

The second target substance detection material of the present invention includes a target substance detection material, a first target substance capturing unit, a second target substance capturing unit, a metal structure, and a polymer matrix.

Figure 1:
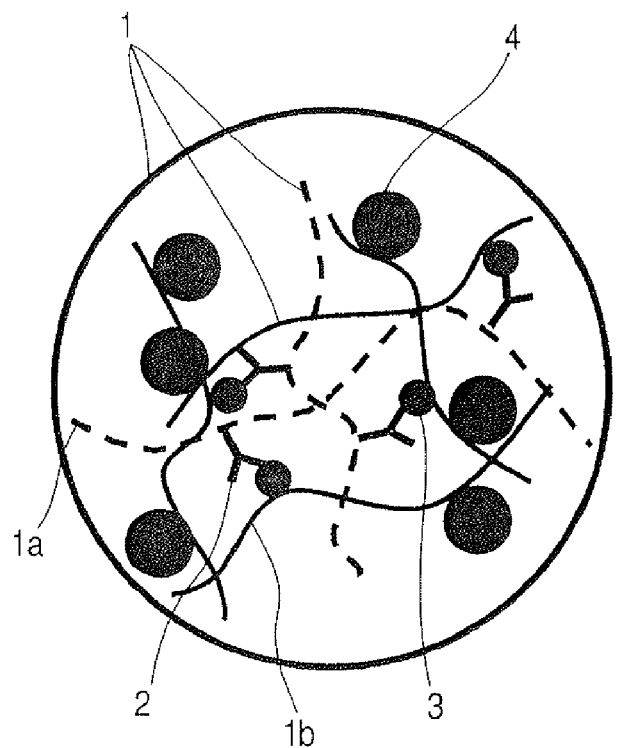
FIG. 1 is a schematic view illustrating the first target substance detection material of the present invention.

FIG. 1 is a typical schematic view illustrating the first target substance detection material of the present invention. The first target substance detection material includes at least a target substance capturing unit 2, a capturing unit binding substance 3, a metal structure 4, and a polymer matrix 1. The target substance capturing unit 2 and the capturing unit binding substance 3 are immobilized on different portions of the polymer matrix. More specifically, the target substance capturing unit 2 is immobilized on a polymer chain A (1a in the figure) among polymer chains that constitute the polymer matrix 1. The capturing unit binding substance 3 is immobilized on a polymer chain B (1b in the figure) among polymer chains that constitute the polymer matrix 1.

The polymer matrix 1 has a three-dimensional crosslinked structure (network structure) consisting of polymer chains. Since the crosslinked portion formed with polymer chains is small, the above polymer matrix contains moisture that is obtained from an aqueous solution, and thus it swells.

The target substance capturing unit 2, which is immobilized on the polymer chain A in the polymer matrix 1, captures the capturing unit binding substance 3, which is immobilized on the polymer chain B in the polymer matrix 1. Thus, the target substance capturing unit 2 reversibly binds to the capturing unit binding substance 3. That is to say, the target substance capturing unit 2 and the capturing unit binding substance 3 form a complex (hereinafter referred to as a "target substance capturing unit 2—capturing unit binding substance 3 complex", at times). When compared with a state where the target substance capturing unit 2 and the capturing unit binding substance 3 do not form such a complex, the polymer matrix 1 is retained in a relatively contracted state as a result of such a bond. Hereinafter, a state where the above complex is formed is referred to as a state where a pseudo crosslink is formed, and a state where the above complex is not formed is referred to as a state where a pseudo crosslink is not formed, at times. The polymer chain A on which the target substance capturing unit 2 is immobilized and the polymer chain B on which the capturing unit binding substance 3 is immobilized are preferably different polymer chains, but they may also be an identical polymer chain. If they are an identical polymer chain, in a state where the capturing unit binding substance 3 is not captured by the target substance capturing unit 2, a portion on which the target substance capturing unit 2 is immobilized is apart from a portion on which the capturing unit binding substance 3 is immobilized. The distance between such two portions is greater than the distance obtained by adding the length of the target substance capturing unit 2 to the length of the capturing unit binding substance 3. When the capturing unit binding substance 3 is captured by the target substance capturing unit 2, the distance between the portions, on which these components are immobilized, becomes shorter. Preferably, the distance between the above two portions comes close to the distance that is shorter than the distance obtained by adding the length of the target substance capturing unit 2 to the length of the capturing unit binding substance 3. In order that the target substance capturing unit 2 and the capturing unit binding substance 3 form a conjugate, the polymer chain has an inflection point between a portion on which the target substance capturing unit 2 is immobilized and a portion on which the capturing unit binding substance 3 is immobilized.

The metal structure 4 may be included in the space inside of a three-dimensional crosslinked structure formed by the polymer matrix 1, or may also be immobilized on a polymer chain.

Figure 2A:
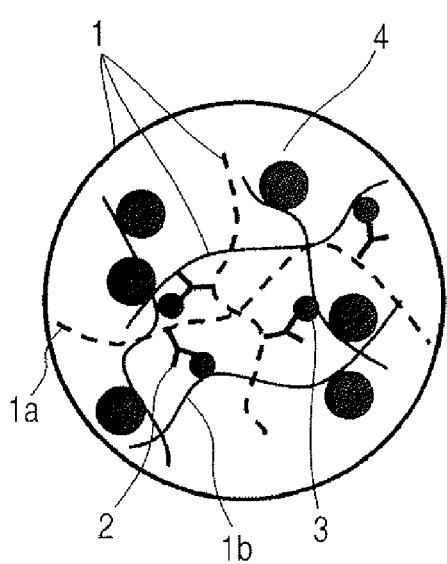
FIGS. 2A and 2B are schematic views illustrating a change occurring when the first target substance detection material of the present invention is allowed to come into contact with a target substance.
Figure 2B:
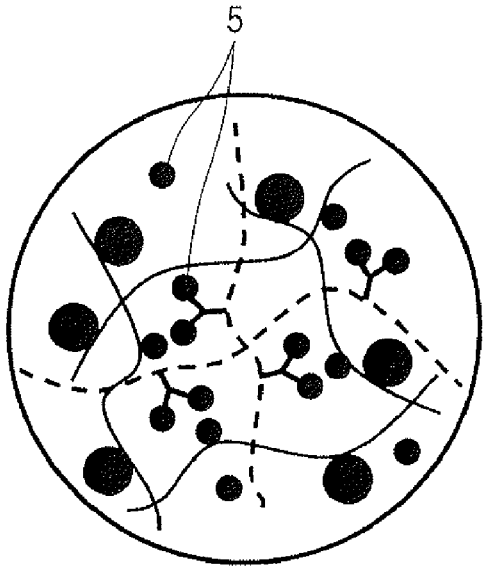

Subsequently, a change generated when a specimen containing the target substance 5 is allowed to come into contact with the first target substance detection material is shown in FIGS. 2A and 2B.

When the specimen containing the target substance 5 is allowed to come into contact with the first target substance detection material, the target substance capturing unit 2, which has formed a complex with the capturing unit binding substance 3 via a specific bond, is released from the capturing unit binding substance 3, and instead, it captures the target substance. That is to say, the target substance capturing unit 2 is released from the bond with the capturing unit binding substance 3, and it binds to the target substance 5. As a result, the bond of the polymer chain A with the polymer chain B, which has been a pseudo crosslink formed due to the bond of the target substance capturing unit 2 with the capturing unit binding substance 3, is dissociated. Thus, the polymer matrix 1 is significantly changed from a relatively contracted state to a swelling state. That is, when compared with a state where no target substances exist, when a target substance exists, the volume of the target substance detection material increases. Thereby, the distance between the metal structures 4 embedded or immobilized in the polymer matrix 1 becomes greater, so that the relative positional relationship between the metal structures can be changed.

Thus, in the first target substance detection material, the volume of the polymer matrix swells as a result of the existence of the target substance. Based on the change in the properties of the metal structure due to such swelling of the volume of the polymer matrix, the presence or absence of the target substance and the concentration thereof are detected.

Figure 3:
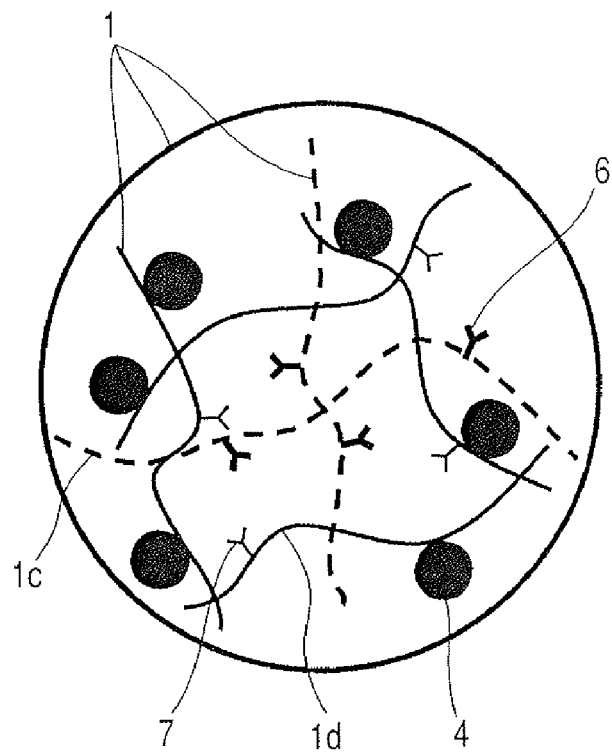
FIG. 3 is a schematic view illustrating the second target substance detection material of the present invention.

Subsequently, a typical schematic view of the second target substance detection material of the present invention is shown in FIG. 3. The second target substance detection material includes at least a first target substance capturing unit 6, a second target substance capturing unit 7, a metal structure 4, and a polymer matrix 1. In addition, the first target substance capturing unit 6 and the second target substance capturing unit 7 are immobilized on different portions of the polymer matrix 1. It is to be noted that the polymer matrix 1 and the metal structure 4 are the same as the polymer matrix and the metal structure of the first target substance detection material of the present invention.

The second target substance detection material of the present invention will be more specifically described. Among polymer chains constituting the polymer matrix 1, the first target substance capturing unit 6 is immobilized on a polymer chain C (1c in the figure), and the second target substance capturing unit 7 is immobilized on a polymer chain D (1d in the figure). The first target substance capturing unit 6 immobilized on the polymer chain C constituting the polymer matrix 1 and the second target substance capturing unit 7 immobilized on the polymer chain D constituting the polymer matrix 1 have capturing sites for recognizing different regions of the target substance 5 and capturing (binding to) the different regions (the details will be described later). It is to be noted that the "immobilization" can be carried out herein via a covalent bond.

Moreover, the polymer chain C on which the target substance capturing unit 6 is immobilized and the polymer chain D on which the target substance capturing unit 7 is immobilized are preferably different polymer chains, but they may also be an identical polymer chain. If they are an identical polymer chain, as in the case of the first target substance detection material, in order that the first target substance capturing unit 6, the target substance 5, and the second target substance capturing unit 7 form a complex (hereinafter referred to as "first target substance capturing unit 6—target substance 5—second target substance capturing unit 7" at times), the polymer chain has an inflection point between a portion on which the first target substance capturing unit 6 is immobilized and a portion on which the second target substance capturing unit 7 is immobilized.

Figure 4A:
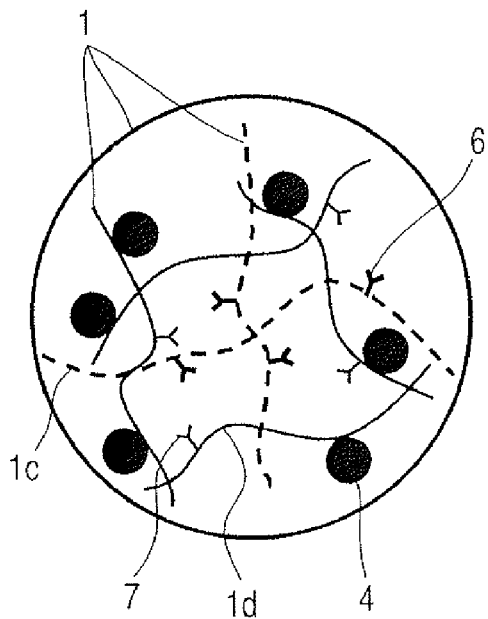
FIGS. 4A and 4B are schematic views illustrating a change occurring when the second target substance detection material of the present invention is allowed to come into contact with a target substance.
Figure 4B:
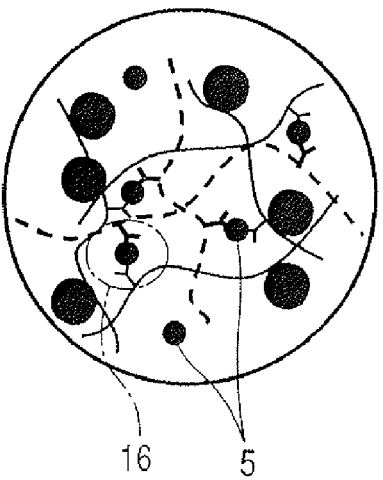

Subsequently, a change generated when a specimen containing a target substance is allowed to come into contact with the second target substance detection material is shown in FIGS. 4A and 4B.

When a solution containing the target substance 5 is allowed to come into contact with the second target substance detection material, the first target substance capturing unit 6 and the second target substance capturing unit 7 recognize different regions of a single target substance 5 and capture them, so as to form a complex 16 consisting of the first target substance capturing unit 6—the target substance 5—the second target substance capturing unit 7. That is to say, the target substance 5 is sandwiched between the first target substance capturing unit 6 and the second target substance capturing unit 7 in a sandwiched manner, and thus the target substance 5 is captured by the first target substance capturing unit 6 and the second target substance capturing unit 7. As a result, a pseudo crosslink is formed between the polymer chain C on which the first target substance capturing unit 6 is immobilized, and the polymer chain D on which the second target substance capturing unit 7 is immobilized. Thus, the second target substance detection material is changed from a relatively swelling state to a contracted state. As a result, the relative positional relationship among several metal structures 4 embedded or immobilized in the polymer matrix is changed.

Thus, in the case of the second target substance detection material, the volume of the polymer matrix is contracted due to the existence of the target substance, and the properties of the metal structure are thereby changed. The presence or absence of the target substance and the concentration thereof are detected by such a change in the properties of the metal structure.

When the first target substance capturing unit 6 and the second target substance capturing unit 7 capture the target substance 5, the target substance 5 captured by the first target substance capturing unit 6 may be further captured by the second target substance capturing unit 7, or the target substance 5 captured by the second target substance capturing unit 7 may be further captured by the first target substance capturing unit 6. Moreover, the first target substance capturing unit 6 and the second target substance capturing unit 7 may simultaneously capture the target substance 5.

The term "relatively" in the expressions "relatively swelling state" and "relatively contracted state" is used based on the comparison between a case where the target substance is present and a case where the target substance is absent.

As described in the "Description of the Related Art" section, a metal structure such as a fine metal particle having a diameter between several nanometers and several hundreds of nanometers, such as a fine gold or silver particle, absorbs light with a certain wavelength ranging from visible to near infrared region by an optical effect known as localized surface plasmon resonance (hereinafter referred to as LSPR at times). It has been known that the wavelength of such light absorbed by LSPR is changed depending on the distance between the metal structures. On the other hand, it is considered that contraction or swelling of the polymer matrix as shown in the above FIGS. 2A, 2B, 4A and 4B occurs in proportion to the concentration of the target substance in a specimen, if conditions for allowing the polymer matrix including the metal structure to come into contact with the specimen are kept constant.

Such an expression "contact conditions are kept constant" is used herein to mean that a state, wherein the target substance sufficiently and uniformly arrives at the inside of the three-dimensional crosslinked structure of the polymer matrix as a result of stirring or adequate heating, is kept. Accordingly, a change in the distance between the metal structures, such as contraction of the polymer matrix in the case of the first target substance detection material or the swelling of the polymer matrix in the case of the second target substance detection material, can be measured as a change in the absorption spectrum of a target substance detection material before and after the contact with the specimen. By measuring such a change in an absorption spectrum, the concentration of the above described target substance in the specimen can be detected.

Moreover, another factor for causing a change in the absorption wavelength of the metal structure before and after the contact with the specimen is a change in the refractive index of the target substance detection material itself obtained when the swelling or contraction of the above material occurs due to the presence or absence of the target substance or the concentration thereof. It has been known that the obtained absorption spectrum changes due to a change in the refractive index around the metal structure in LSPR. Accordingly, a change in the refractive index generated as a result of the swelling or contraction of the above material depending on the presence or absence of the target substance or the concentration thereof according to the present method is measured as a change in the absorption wavelength of the metal structure based on LSPR, so that the presence or absence of the target substance or the concentration thereof can be detected.

Thus, as stated above, the target substance detection material of the present invention can detect the presence or absence of a target substance or the concentration thereof based on (1) a change in the distance between metal structures, or (2) a change in the refractive index around such a metal structure. Which of these (1) and (2) has a greater influence depends on the density of the metal structure existing in the target substance detection material, namely, the positional relationship of the metal structure in an initial state (a state before allowing the detection material to come into contact with a specimen). When the density of metal structures is high and the range of an effective electromagnetic field derived from the localized plasmon of one metal structure is overlapped with the range of an electromagnetic field of an adjacent metal structure, if such metal structures are sufficiently close to each other, a change in the distance between metal structures described in (1) above has a greater influence. On the other hand, when the density of metal structures is low and there are no overlapped portions between the two above effective electromagnetic fields, and thus when the metal structures are sufficiently apart from each other, a change in the refractive index around such a metal structure described in (2) above has a greater influence. In embodiments as given later, the former, that is, as described in (1) above, the case where a change in the distance between metal structures has a greater influence, will be described.

In the case of carrying out such detection, it is preferable that a change in the volume of a target substance detection material due to influences other than the influence due to the target substance be subtracted from a change in the volume of the target substance detection material due to the contact with a specimen. In such a case, the signal of optical properties obtained by allowing a buffer solution containing a specimen, and more preferably a solution containing a specimen excluding the target substance, to come into contact with the target substance detection material, can be used as a control, and the above signal can be subtracted.

The target substance detection material used as a control is preferably a target substance detection material obtained before allowing it to come into contact with a specimen. However, differing from a target substance detection material to be allowed to come into contact with a specimen, a material used as a control may be prepared separately.

When the concentration of the target substance is detected, using standard specimens containing several target substances having known concentrations, the relationship between a change in the spectrum and the concentration of a target substance has been obtained in advance. A calibration curve is produced based on the above relationship, and the function of the change in the spectrum and the concentration of the target substance is then obtained. Using such a function, the concentration of a target substance with an unknown concentration can be obtained based on such a change in the spectrum during the actual measurement. Herein, a change in the spectrum may be either a change in the wavelength having the maximum value of strength (a change in the spectrum peak), or a change in the peak form such as a half width of the spectrum peak. Further, a change in the strength of light at one or several wavelengths may also be used.

Next, a target substance and elements constituting a target substance detection material (a polymer matrix, a metal structure, a capturing unit binding substance, and a target substance capturing unit) will be described in detail.

<Polymer Matrix>

The polymer matrix 1 has a three-dimensional crosslinked structure (network structure) of polymer chains. The polymer matrix includes a target substance capturing unit and a metal structure, and has a function as a support therefor. In addition, since the polymer matrix 1 has only a few crosslinked portions between polymer chains that constitute the polymer matrix, it is able to contain a solution therein. Moreover, the above polymer matrix has flexibility, to such an extent that a pseudo crosslinked structure is formed as a result of a specific interaction between substances immobilized on the surface of a polymer chain, so that the volume thereof can be changed.

As such a polymer matrix 1, any substance can be used, as long as it has the aforementioned properties, and it does not affect the binding reaction of a target substance capturing unit with a target substance (or a capturing unit binding substance).

A solvent for a solution contained in the polymer matrix 1 may be either hydrophilic or hydrophobic. Moreover, it is necessary for the polymer matrix 1 to have an appropriate permeability of a wavelength region for evaluating the optical properties of a metal structure. Accordingly, it is preferable that crosslinked portions be homogeneously present. Furthermore, it is also preferable that the polymer matrix 1 have functional groups for immobilizing the above target substance capturing unit, capturing unit binding substance, and metal structure on the side chain thereof. When a functional group allowed to react with the groups of such a target substance and capturing unit binding substance is formed in a polymer chain, a monomer having the above function group may be mixed into the polymer chain at the stage of polymerization of the monomer, so as to form a polymer chain having the above functional group. Otherwise, a monomer may be polymerized to form a polymer chain, and thereafter, a chemical modification may be performed on the above polymer chain, so as to form the above functional group.

The polymer matrix 1 may be produced such that it forms a microsphere. In such a case, each monomer precursor that forms a polymer chain may be encapsulated into a capillary, and polymerization may be then carried out in the capillary.

When a target substance exists in an aqueous medium (hydrophilic medium) and the binding reaction of the target substance to a target substance capturing unit is also carried out in the aqueous medium, a polymer hydrogel (which may be simply referred to as a "hydrogel", but this hydrogel means the same above polymer hydrogel) can be used as the polymer matrix 1. The term "polymer hydrogel" is used in the present invention to mean a gel, which has a network structure (three-dimensional crosslinked structure) formed by intertwining hydrophilic polymer chains, and which contains moisture in an aqueous solution and thereby swells to a certain volume.

Water molecules in the gel are classified into several states (combined water, bound water, and free water) depending on the difference in the strength of the interaction between the water molecules and polymer chains in the gel. In general, when the percentage by weight of free water contained in a gel that is calculated relative to the value obtained by the DSC (differential scanning calorimetry) measurement or TG-DTA (thermogravimetry/differential thermal analysis) measurement is 30% to 50% or more, such a gel is called a hydrogel (R. M. Hodge et al., Polymer, 37, 1371 (1996), W.-Z. Zhang et al., J. Membrane Sci., 42, 303 (1989)). The percentage by weight of the hydrogel used in the present invention is 80% or more based on the weight of a polymer chain contained in an aqueous solution. In general, it is preferable to use 90% or more by weight of the hydrogel. Such a hydrogel can be formed by mixing a cross-linker into a monomer before polymerization, at a weight ratio of 3% or less based on the weight of the monomer. The degree of swelling/contraction of the polymer hydrogel due to the contact with the above target substance is determined based on the degree of crosslinking between polymer chains. Thus, such polymer chains should be designed at an appropriate crosslink density, depending on the type of a specimen or detection conditions. In addition, the expression "hydrogel has hydrophilicity" is used in the present invention to mean that when the hydrogel is allowed to come into contact with a sufficient amount of an aqueous solution, the hydrogel absorbs water and is then hydrated, so that the hydrogel has the property of being suspended in the water in a colloidal state or dissolved therein.

Examples of such a polymer hydrogel include polymers such as polyacrylic acid, polyacrylic ester, polyacrylamide, or the derivative thereof. Moreover, if the aforementioned conditions are satisfied, other polymers that are generally used as "polymer hydrogels", such as polyamino acid or polyvinyl alcohol, can also be used. Furthermore, an alloy or copolymer thereof can also be used.

Contraction or swelling of the polymer matrix can be confirmed with an optical microscope.

<Metal Structure>

The metal structure of the present invention can be formed using any type of metal, as long as the used metal has a region for absorbing light due to a plasmon resonance phenomenon. Such a metal having a light absorption region due to such a plasmon resonance region is selected from the group consisting of gold, silver, copper, aluminum, and an alloy containing these metals. Of these, gold or silver is preferably used, taking into consideration the properties of a plasmon resonance phenomenon or processability. In particular, in the case of a reaction performed in an aqueous solution containing salts, gold is preferably used because it hardly deteriorates. It is to be noted that there are cases where the metal structure is described as a metal-containing structure in the present specification.

In addition, such a metal structure may be a laminated structure comprising several layers. In the case of adopting such a laminated structure, if the outermost layer comprises a metal having a light absorption region due to the plasmon resonance phenomenon, other layers may comprise materials having no light absorption regions due to the plasmon resonance phenomenon. Such a material having no light absorption regions due to the plasmon resonance phenomenon may be either a metal, or a dielectric such as a polymer material or inorganic material. An example of such a material is a so-called dielectric-metal core shell structure, which is formed by coating a polystyrene polymer or a silica material with a thin gold film in order to improve the performance of plasmon resonance.

The shape of the metal structure may be spherical, pyramidal, or acicular. In addition, the above metal structure may also be a structure obtained by distortion of the above shapes, or an asymmetric structure. Thus, the shape of the metal structure is not limited. The metal structure should have a size necessary for the occurrence of a plasmon resonance phenomenon in a region ranging from a visible region to a near infrared region (which is a region having an absorption wavelength between 450 nm and 1,500 nm). Thus, when the metal structure has a spherical shape, the diameter thereof is preferably between 5 nm and 500 nm. When the metal structure has a rod shape, the major axis thereof is preferably between 20 nm and 500 nm. In the case of a projection-shaped structure (which is a structure having a cluster of a certain size, which has another cluster that is smaller than the above cluster at a portion of the surface thereof or on the entire surface thereof), a core structure having a size between 5 nm and 500 nm preferably has a projection structure having a size between 1 nm and 50 nm.

As far as the metal structure is immobilized on a polymer chain, it may be physically (via non-covalent bond) embedded in a space of the three-dimensional crosslinked structure of the polymer chain that constitutes the polymer matrix 1. Otherwise, the metal structure may also be immobilized on the main chain or side chain of the polymer chain via a certain molecule or directly via covalent bond. Further, the metal structure may also be immobilized as a result of adsorption on the polymer chain. When the metal structure comprises gold, a portion of the polymer chain is allowed to retain a thiol group or an amino group, so that the metal structure can be preferably immobilized on the polymer chain due to the bonding power of gold—the thiol group or gold—the amino group.

<Target Substance, Capturing Unit Binding Substance, Target Substance Capturing Unit>

Next, a target substance, a capturing unit binding substance, and a target substance capturing unit will be described.

First, the capturing unit binding substance (capturing molecule binding substance) will be described using FIGS. 1, 2A, and 2B.

As described above, the capturing unit binding substance 3 of the first target substance detection material is immobilized on the polymer chain B (1b) of the polymer matrix 1. The above capturing unit binding substance forms a reversible bond together with the target substance capturing unit 2 immobilized on the polymer chain A (1a) via a specific affinity (bonding power) as described later (FIG. 1). By allowing the capturing unit binding substance 3 and the target substance capturing unit 2 to come into contact with target substance 5 in such a state, the bond of the capturing unit binding substance 3 to the target substance capturing unit 2 is dissociated, and instead, the bond of the target substance 5 to the target substance capturing unit 2 is formed. Herein, a specific bond means a unique bond between specific substances, such as a biological material interaction, as described later.

The capturing unit binding substance 3 for generating such a phenomenon can be selected from the group consisting of substances, which have a specific bonding power to the target substance capturing unit 2, but which the affinity of the capturing unit binding substance 3 with the target substance capturing unit 2 obtained in a state where the capturing unit binding substance 3 is immobilized on the polymer matrix 1 is lower than the affinity of the target substance capturing unit 2 with the target substance 5 obtained in a state where the target substance capturing unit 2 is immobilized on the polymer matrix 1. In order to satisfy such conditions, the dissociation constant (hereinafter referred to as Kd at times) between the capturing unit binding substance 3 and the target substance capturing unit 2 in the state where the capturing unit binding substance 3 is not immobilized on the polymer matrix 1 is preferably greater than the dissociation constant between the target substance 5 and the target substance capturing unit 2. More preferably, the dissociation constant between the capturing unit binding substance 3 and the target substance capturing unit 2 is 10 or more times greater than the dissociation constant between the target substance 5 and the target substance capturing unit 2. There are cases where the aforementioned conditions are satisfied, although the dissociation constant between the target substance capturing unit 2 and the capturing unit binding substance 3 that is not immobilized on the polymer matrix 1 is smaller than or equivalent to the dissociation constant between the target substance capturing unit 2 and the target substance 5. This is because the dissociation constant between the capturing unit binding substance 3 and the target substance capturing unit 2 is considered to be increased by immobilization of the capturing unit binding substance 3 on the polymer matrix 1. Accordingly, as a capturing unit binding substance having the same dissociation constant, a molecule that is completely identical to the target substance can also be used (described in Embodiments below).

Such a capturing unit binding substance 3 can be formed by structurally or chemically deforming, mutating, or modifying the target substance, and preferably has the affinity with the target substance capturing unit 2 under the aforementioned conditions. In a case where a target molecule (target substance) is nucleic acid, an example of such a capturing unit binding substance is a target substance analog having a mismatch sequence consisting of one to several nucleotides.

To sum up, a molecule, which has a Kd value between the above molecule and the target substance capturing unit 2 that is greater than a Kd value between the target substance 5 and the target substance capturing unit 2, can be preferably used as the capturing unit binding substance 3. In addition, even using, as the capturing unit binding substance 3, a molecule having a Kd value between the above molecule and the target substance capturing unit 2 that is smaller than a Kd value between the target substance 5 and the target substance capturing unit 2, if the affinity of the above molecule with the target substance capturing unit 2 immobilized on a polymer chain is lower than the affinity of the target substance 5 with the target substance capturing unit 2, such a molecule can be used without problems.

Next, a target substance capturing unit and a target substance will be described using FIGS. 2A, 2B, 4A, and 4B.

The target substance capturing unit 2 in the first target substance detection material of the present invention may have the aforementioned relationship with the target substance 5 and the capturing unit binding substance 3.

The first target substance capturing unit 6 and the second target substance capturing unit 7 in the second target substance detection material of the present invention have capturing sites for recognizing each different regions of the target substance 5 and capturing them.

Moreover, a case where the first target substance capturing unit 6 and the second target substance capturing unit 7 have a single capturing site and where the above capturing site is able to capture several regions of the target substance 5, may also be included in the concept that "the first target substance capturing unit 6 and the second target substance capturing unit 7 have capturing sites for recognizing each different regions of the target substance 5 and capturing them". In such a case, there may be a case where the first target substance capturing unit 6 captures a specific region among several regions of the target substance 5 and where the second target substance capturing unit 7 captures any one region of the above several regions other than the region captured by the first target substance capturing unit 6. Accordingly, the first target substance capturing unit and the second first target substance capturing unit may be the same capturing unit, as long as the unit is able to capture several regions of the target substance 5.

Examples of the relationship between the target substance and the target substance capturing unit include the relationship of an antigen—an antibody, the relationship of DNA or RNA-DNA or RNA (hybridization), the relationship of a ligand—a receptor, the relationship of DNA or RNA such as a transcription factor—a protein, the relationship of an enzyme—a substrate, and the relationship of a sugar chain compound—a protein (lectin). The type of such a relationship is not particularly limited, as long as it is a relationship having a specific bond. Thus, the relationship between the target substance and the target substance capturing unit satisfies the aforementioned relationships. When the relationship of the target substance—the target substance capturing unit is indicated as α-β, the combination of α with β shows both a case where the target substance is α and the target substance capturing unit is β, and a case where the target substance is β and the target substance capturing unit is α.

Figure 7:
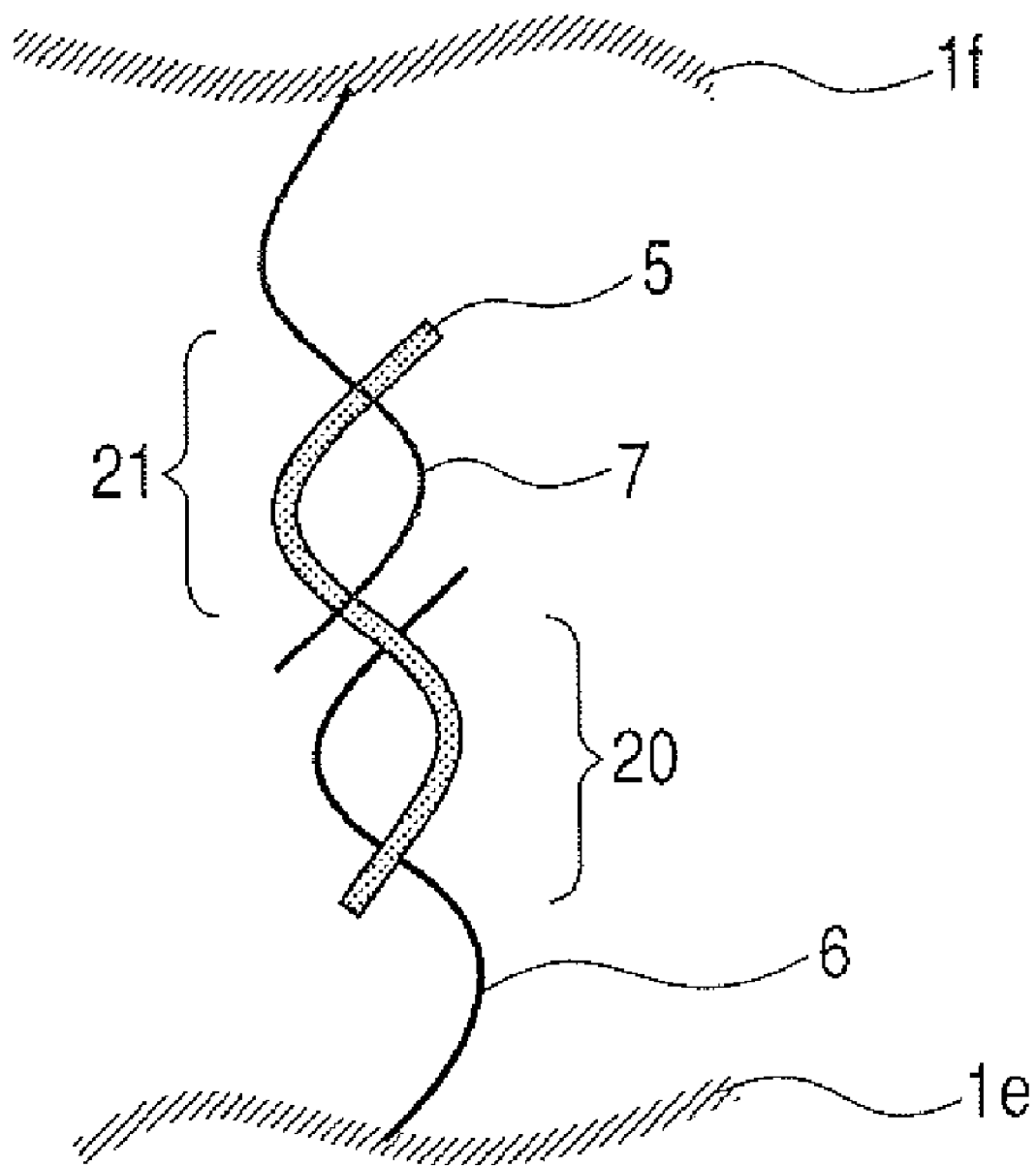
FIG. 7 is a schematic view illustrating reaction examples of a target substance and first and second target substance capturing units, when the target substance and the first and second target substance capturing units are nucleic acids.

When the target substance 5, the first target substance capturing unit 6, and the second target substance capturing unit 7 are nucleic acids, the reaction examples of the above first target substance capturing unit, the above second target substance capturing unit, and the above target substance are shown in FIG. 7. The target substance 5 that is nucleic acid (DNA or RNA) binds to nucleic acid that is the first target substance capturing unit 6 immobilized on the polymer chain E (1e in the figure) in a first complementary sequence region 20 among the sequences of the target substance 5. The target substance 5 also binds to the second target substance capturing unit 7 immobilized on the polymer chain F (1f in the figure) in a second complementary region 21 that is different from the first complementary sequence region 20 among the sequences of the target substance 5, so as to make a complementary bond. In such a case, the nucleic acid sequence of the first target substance capturing unit and that of the second target substance capturing unit are designed, synthesized, and used, such that the nucleic acid sequence of the first target substance capturing unit and that of the second target substance capturing unit do not overlap each other.

When the target substance is an antigen and the target substance capturing unit is an antibody, the combination of a capture antibody with a labeled antibody used in the ELISA method or the like can be used as the first target substance capturing unit and the second target substance capturing unit. Antibodies that are commercially available in an ordinary ELISA kit can be used.

When the combination of the target substance and the target substance capturing unit is an antigen—an antibody, a wide range of antigens including organism cells such as bacteria, virus, a protein (including a so-called disease marker), a gene fragment, a peptide, an endocrine disrupting chemical (environmental hormone), dioxin, and a low molecular weight compound such as PCB, can be used.

In addition, any type of molecule can be used as an antibody, as long as it includes a region having a so-called immunoglobulin fold structure. In general, an antibody itself such as IgG, IgM, IgA, IgE or IgD, and a complex thereof, can be used. In addition, a fragment thereof such as Fab'2, Fab, or Fv can also be used. Further, VH or VL can also be used singly.

Furthermore, an antibody fragment complex formed by converting the above components to a single strand with a peptide linker by genetic engineering, such as scFv, Diabody, Triabody, or Tetrabody, can also be used.

These target substance capturing unit and capturing unit binding substance are immobilized on a polymer chain via a covalent bond, an ionic bond, or adsorption, for example. However, immobilization methods are not limited thereto, as long as these components are favorably immobilized or deposited on the polymer chain.

As a method of immobilizing the target substance capturing unit and the capturing unit binding substance on a polymer chain via a bond, a method, which comprises forming a functional group having a succinimide skeleton on a polymer chain and allowing the aforementioned functional group having such a succinimide skeleton to react with the amino groups of the target substance capturing unit and capturing unit binding substance, can be applied, for example. In addition, there is also applied a method, which comprises forming a functional group having a maleimide skeleton on a polymer gel molecular chain and allowing the functional group to react with the thiol groups of the target substance capturing unit and capturing unit binding substance. Herein, the amino groups and thiol groups of the target substance capturing unit and capturing unit binding substance may be originally present in molecules, or may be obtained as a result of chemical modification.

In order to more precisely adjust the frequency of immobilization of the target substance capturing unit and the capturing unit binding substance in a polymer chain, the following method can be used. First, the target substance capturing unit and the capturing unit binding substance are modified with a monomer precursor of the polymer chain that forms a hydrogel. Thereafter, the monomer precursor-modified target substance capturing unit and the monomer precursor-modified capturing unit binding substance are directly polymerized. In this method, the additive ratio of the monomer precursor-modified target substance capturing unit and the monomer precursor-modified capturing unit binding substance to a common monomer precursor is adjusted, so as to adjust the frequency of immobilization of the target substance capturing unit and the capturing unit binding substance in the polymer chain.

Moreover, a target substance detection kit and a target substance detection element can be produced using the above target substance detection material. Such a target substance detection kit and a target substance detection element will be described using FIGS. 5 and 6.

Figure 6:
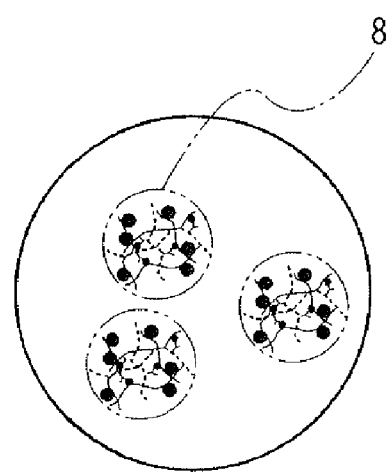
FIG. 6 is a schematic view illustrating the state of a target substance detection material in a solution of the kit as shown in FIG. 5.

The target substance detection kit using the target substance detection material is a kit for detecting the presence or absence of the target substance in a specimen and/or the concentration thereof. The target substance detection kit includes the above first or second target substance detection material 8 and a vessel 10 for allowing a specimen containing the above target substance to come into contact with the target substance detection material. The state of the target substance detection material 8 in a solution 9 containing the above target substance detection material 8 is schematically shown in FIG. 6.

Furthermore, the target substance detection element using the target substance detection material is an element for detecting the presence or absence of the target substance in specimen and/or the concentration thereof. The above target substance detection element is characterized in that it includes a specimen contact vessel 10 that is a region for introducing the first or second target substance detection material 8 of the present invention and the above specimen and also for allowing the specimen containing the above target substance to come into contact with the target substance detection material, and wavelength light transmitting regions 17 and 18 used for measuring the optical properties of the above target substance detection material. Herein, the wavelength light transmitting region 17 is a region, into which light of a plane close to light source transmits, among the planes of the specimen contact vessel 10 intersecting with an incident light 14. The wavelength light transmitting region 18 is a region, into which light of a plane diagonally opposed to the above plane among the planes of the specimen contact vessel 10.

The solution 9 containing the target substance detection material 8 is stored in the vessel (specimen contact vessel) 10 containing a region for allowing a specimen to come into contact with the target substance detection material 8. Thereafter, a specimen 11 used to detect the presence or absence of a target substance or the concentration thereof is introduced into the above specimen contact vessel 10 from the outside.

Figure 5:
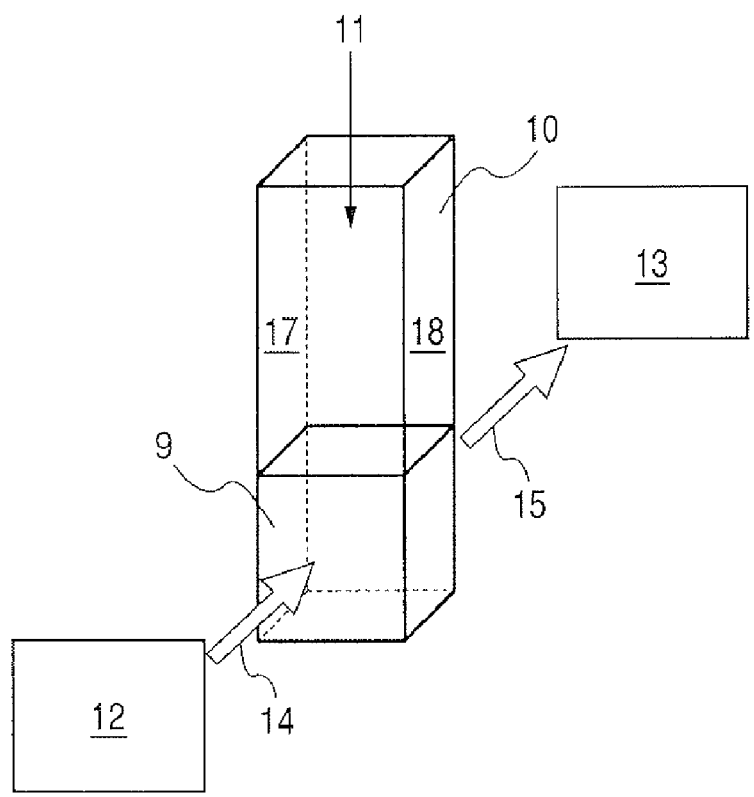
FIG. 5 is a schematic view illustrating a kit and an element, which include a target substance detection material.

Thereafter, from the light source 12, the incident light 14 that has passed through the light transmitting region 17 is allowed to enter into the specimen 11 and the solution 9 containing the target substance detection material 8 inside the specimen contact vessel 10, and transmitted light 15 passed through the above solution is detected with a detector 13. In FIG. 5, a vessel for storing the target substance detection material is identical to the contact vessel. However, such a vessel for storing the target substance detection material may also be prepared, separately. In addition, since the transmitted light 15 is configured to be detected in FIG. 5, regions 17 and 18 are defined as wavelength transmitting regions. However, the region 17 can be defined as a transmitting region. The plane on which the region 17 exists can be defined as a reflection plane, so that the above wavelength transmitting region 18 can be defined as a reflection region. In such a case, seeing from the specimen contact vessel 10, the detector 13 and the light source 12 are in the same direction, so that the detector is configured to detect reflection light.

EMBODIMENTS

The present invention will be described more in detail in the following embodiments. However, these embodiments are not intended to limit the present invention. Various changes and modifications may be made regarding materials, composition conditions, reaction conditions, or the like, to such an extent that a detection material, a detection kit, and a detection element having the same functions and effects can be obtained.

Embodiment 1

Example of first target substance detection material

In Embodiments 1 and 2, bovine serum albumin (hereinafter referred to as BSA at time) is used as a target substance and a capturing unit binding substance, and a goat anti-BSA immunoglobulin G monoclonal antibody (hereinafter referred to as anti-BSA-GIgG at times) is used as a target substance capturing unit.

<Synthesis and Purification of Capturing Unit Binding Substance—and Target Substance Capturing Unit-monomer Precursors>

The present synthesis and purification are carried out according to the method described in Appl. Biochem. Biotech., 15, 11-24 (1987) and Nature, 399, 766-769 (1999). That is to say, 0.4 mg of N-succinimidyl acrylate (hereinafter referred to as NSA at times) is added to a phosphate buffer (20 mM, pH 7.4) containing 100 mg of anti-BSA-GIgG used as a target substance capturing unit, and the obtained mixture is reacted at 36° C. for 1 hour. Thereafter, purification is carried out by gel filtration. The same synthesis and purification are performed on BSA used as a capturing unit binding substance, using a molar ratio that is appropriate to NSA, so as to obtain an anti-BSA-GIgG-monomer precursor and a BSA-monomer precursor from each step.

<Polymerization and Synthesis of Capturing Unit Binding Substance—and Target Substance Capturing Unit-immobilized Polymer Chains>

Subsequently, 30 mg of acrylamide (hereinafter referred to as AAm at times) is added to 570 mg of the anti-BSA-GIgG-monomer precursor. Thereafter, 0.01 ml of an ammonium persulfate (hereinafter referred to as APS at times) aqueous solution (100 mM) and 0.01 ml of N, N,N',N'-tetramethylethylenediamide (hereinafter referred to as TEMED at times) (0.8 M) are further added thereto. The obtained mixture is reacted at 25° C. for 3 hours, so as to obtain an anti-BSA-GIgG-immobilized polymer chain having a molecular weight of approximately 200,000. The same polymerization reaction is performed on BSA used as a capturing unit binding substance, using a molar ratio that is appropriate to each reagent, so as to obtain a BSA-immobilized polymer chain.

<Synthesis of Capturing Unit Binding Substance—and Target Substance Capturing Unit-immobilized Polymer Hydrogels>

The BSA-immobilized polymer chain (2.5 mg) obtained as described above, 85 mg of AAm, and N,N'-methylenebisacrylamide (hereinafter referred to as MBAA at times) (0.1% by weight based on the weight of AAm) are dissolved in 600 mg of a phosphate buffer that contains the obtained anti-BSA-GIgG-immobilized polymer chain and a fine gold colloidal particle having a diameter of 40 nm. Thereafter, 0.01 ml of an APS aqueous solution (100 mM) and 0.01 ml of a TEMED aqueous solution (0.8 M) are added to the solution, and the obtained solution is immediately introduced in a glass capillary. Thereafter, a crosslinking reaction is carried out at 25° C. for 3 hours. After completion of the reaction, the obtained hydrogel is immersed in a phosphate buffer.

At the same time, a hydrogel containing only polyacrylamide, which is used as a control, is also synthesized by the same above method with the exception that neither a capturing unit binding substance nor a target substance capturing unit is added.

Embodiment 2

An example of target substance detection method using target substance detection material of Embodiment 1

500 μl of the polymer hydrogel-phosphate buffer aqueous solution obtained in Embodiment 1, on which the capturing unit binding substance and the target substance capturing unit have been immobilized, is placed in a quartz optical cell, and the absorption spectrum thereof is obtained in advance using a visible/near infrared spectrophotometer. At the same time, a hydrogel dispersion containing only polyacrylamide is used as a control, and the absorption spectrum thereof is also obtained. Thereafter, 50 μl of BSA-containing phosphate buffers each having a concentration of 50 μg/ml, 100 μg/ml, or 500 μg/ml, are successively added to these cells. Two hours after the addition, an absorption spectrum is obtained. As a result, the absorption spectrum of the hydrogel dispersion containing only polyacrylamide used as a control is hardly changed. In contrast, in the case of the absorption spectrum of the capturing unit binding substance—and the target substance capturing unit-immobilized polymer hydrogel dispersion, the maximum absorption wavelength shifts to the long wavelength side, as the BSA solution is added.

Embodiment 3

Example of second target substance detection material

In Embodiments 3 and 4, BSA is used as a target substance, a goat anti-BSA immunoglobulin G monoclonal antibody (hereinafter referred to as anti-BSA-GIgG at times) is used as a first target substance capturing unit, and a rabbit anti-BSA immunoglobulin G monoclonal antibody (hereinafter referred to as anti-BSA-GIgG at times) is used as a second target substance capturing unit.

<Synthesis of the First Target Substance Capturing Unit—and the Second Target Substance Capturing Unit-immobilized Polymer Hydrogels>

The polymer hydrogels, on which the first target substance capturing unit and the second target substance capturing unit have been immobilized, are obtained by the same method as that described in Embodiment 1 with the exception that anti-BSA-RIgG is used instead of BSA of Embodiment 1.

Embodiment 4

An example of target substance detection method using target substance detection material of Embodiment 3

Using the polymer hydrogel-phosphate buffer aqueous solution obtained in Embodiment 3, on which the first target substance capturing unit and the second target substance capturing unit have been immobilized, and a hydrogel dispersion containing only polyacrylamide, BSA used as a target substance is detected in the same manner as that described in Embodiment 2.

As a result, the absorption spectrum of the hydrogel dispersion containing only polyacrylamide used as a control is hardly changed. In contrast, in the case of the absorption spectrum of the first target substance capturing unit- and the second target substance capturing unit-immobilized polymer hydrogel dispersion, the maximum absorption wavelength shifts to the short wavelength side, as the BSA solution is added.

Embodiment 5

Another Example of the first target substance detection material

In Embodiment 5, as an example that is different from the first target substance detection material of Embodiment 1, an example of a target substance detection material wherein gold colloid is immobilized on a polymer chain will be given.

First, in order to prepare solution 1, 0.5 g of glycidyl methacrylate (hereinafter referred to as GMA at times) and 7 g of acetone are weighed and are then placed in a reactor. Thereafter, oxygen contained in the reactor and in the solution is substituted with nitrogen via nitrogen bubbling.

Second, in order to prepare solution 2, 0.05 g of 2,2'-azobis (2-methylpropanenitrile) (hereinafter referred to as AIBN at times) used as a polymerization initiator is dissolved in 3 g of acetone. Thereafter, oxygen contained in the solution is substituted with nitrogen via nitrogen bubbling.

Subsequently, the temperature of solution 1 is kept at 60° C. Solution 2 is poured into the reactor using a syringe, while stirring, so as to initiate polymerization. One hour after the polymerization, air (oxygen) is placed in the reactor, so as to terminate the polymerization. For purification, the polymer solution obtained after the polymerization is added dropwise to an excessive amount of methanol, so as to reprecipitate the polymer.

The molecular weight of PolyGMA obtained by the aforementioned operations is measured by GPC. It is found that PolyGMA having a number-average molecular weight (Mn)= approximately 15000, and Mw (weight-average molecular weight)/Mn=approximately 3, is obtained.

A glycidyl group at the terminus of the obtained PolyGMA is converted to an amino group in the following operations. First, 0.02 g of PolyGMA is dissolved in 10 ml of acetone. Separately, aminoethanethiol in an amount that is 20 times the monomer unit of PolyGMA is dissolved in distilled water. Thereafter, using a 1 N NaOH aqueous solution or a 1 N HCl aqueous solution, the pH of the above solution is adjusted to be pH 9.0. The total amount is adjusted to be 70 ml.

Thereafter, these solutions are blended, and the mixed solution is then reacted at room temperature for 24 hours, while stirring. After completion of the reaction, the reaction solution is dialyzed in distilled water and is then purified, so as to obtain an aminated PolyGMA polymer.

Subsequently, the same amount (weight ratio) of the aforementioned aminated PolyGMA polymer is subjected to the same operations as those in the method of synthesizing a hydrogel that is performed in Embodiment 1, so as to obtain a hydrogel material formed by immobilizing a gold colloidal particle on the amino terminus of the aminated PolyGMA polymer.

Embodiment 6

Example of target substance detection method using first target substance detection material of Embodiment 5

The same method as that in Embodiment 2 is carried out with the exception that the hydrogel material obtained in Embodiment 5 is used instead of the hydrogel material of Embodiment 2, so as to detect BSA as a target substance. As a result, there are almost no changes in the absorption spectrum of a hydrogel dispersion containing only polyacrylamide used as a control. In contrast, in the absorption spectrum of a polymer hydrogel dispersion, on which the capturing unit binding substance and the target substance capturing unit are immobilized, the maximum absorption wavelength shifts to the long wavelength side by addition of a BSA solution.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-120480, filed Apr. 25, 2006, which is hereby incorporated by reference herein in its entirety.

What is claimed is:

1. A target substance detection material for detecting a target substance in a specimen, which comprises:
   a plural number of metal structures,
   a polymer matrix having a three-dimensional crosslinked structure including polymer chains,
   a target substance capturing unit capable of binding to the target substance, and
   a capturing unit binding substance capable of reversibly binding to the target substance capturing unit,
   wherein the target substance capturing unit and the capturing unit binding substance are immobilized on different sites on the polymer chains,
   wherein the capturing unit binding substance binds to the target substance capturing unit such that the polymer matrix is retained in a relatively contracted state,
   wherein the capturing unit binding substance is a target substance analogue which can be formed by structurally or chemically deforming, mutating or modifying the target substance,
   wherein the dissociation constant between the target substance capturing unit and the capturing unit binding substance is greater than the dissociation constant between the target substance capturing unit and the target substance, and
   wherein the metal structures are held in the polymer matrix.

2. The target substance detection material according to claim 1, wherein the polymer matrix is comprised of a hydrogel.

3. The target substance detection material according to claim 1, wherein the above immobilization is formed via a covalent bond.

4. The target substance detection material according to claim 1, wherein the dissociation constant between the target substance capturing unit and the capturing unit binding substance is 10 times or more than the dissociation constant between the target substance capturing unit and the target substance.

5. A target substance detection method for detecting a target substance in a specimen, which comprises the steps of:
   bringing a specimen which may contain a target substance into contact with a target substance detection material which comprises a plural number of metal structures, a polymer matrix having a three-dimensional crosslinked structure including polymer chains, a target substance capturing unit capable of binding to the target substance and a capturing unit binding substance capable of reversibly binding to the target substance capturing unit, wherein the capturing unit and the binding substance are immobilized on different sites on the polymer chains, wherein the capturing unit binding substance binds to the target substance capturing unit such that the polymer matrix is retained in a relatively contracted state, wherein the capturing unit binding substance is a target substance analogue which can be formed by structurally or chemically deforming, mutating or modifying the target substance, wherein the dissociation constant between the target substance capturing unit and the capturing unit binding substance is greater than the dissociation constant between the target substance capturing unit and the target substance, and wherein the metal structures arc held in the polymer matrix, to eliminate the binding between the capturing unit binding substance and the target substance capturing unit because of preferential forming of a binding between the target substance capturing unit and the target substance, thereby increasing the volume of the polymer matrix comprised in the target substance detection material and the spacing between the metal structures, and
   detecting a change in localized surface plasmon resonance of the target substance detection material caused by a change in spacing between the metal structures to detect the presence of the target substance in the specimen.

* * * * *